United States Patent [19]
Deem

[11] Patent Number: 6,042,876
[45] Date of Patent: Mar. 28, 2000

[54] GUIDEWIRE HAVING HYDROPHILIC COATING

[75] Inventor: Mark E. Deem, San Francisco, Calif.

[73] Assignee: Medtronic, Inc., Minneapolis, Minn.

[21] Appl. No.: 09/198,190

[22] Filed: Nov. 23, 1998

Related U.S. Application Data

[63] Continuation of application No. 08/665,973, Jun. 21, 1996, Pat. No. 5,840,046.

[51] Int. Cl.[7] .................................. B05D 3/02; B05D 1/00
[52] U.S. Cl. .......................... 427/2.28; 427/2.3; 427/358; 427/434.4; 427/434.6; 427/434.7
[58] Field of Search ..................... 427/358, 2.28, 427/2.1, 117, 118, 120, 178, 434.7, 434.4, 434.6

[56] References Cited

U.S. PATENT DOCUMENTS

| | | | |
|---|---|---|---|
| 3,973,556 | 8/1976 | Fleischhacker et al. | 128/2 M |
| 4,534,363 | 8/1985 | Gold | 128/772 |
| 4,545,390 | 10/1985 | Leary | 128/772 |
| 4,554,929 | 11/1985 | Samson et al. | 128/772 |
| 4,663,233 | 5/1987 | Beavers | 428/412 |
| 4,684,551 | 8/1987 | Vassiliou | 427/434.7 |
| 4,748,986 | 6/1988 | Morrison et al. | |
| 4,801,475 | 1/1989 | Halpern et al. | |
| 4,815,478 | 3/1989 | Buchbinder et al. | 128/772 |
| 4,846,186 | 7/1989 | Box et al. | 128/657 |
| 4,959,074 | 9/1990 | Halpern et al. | 427/2.1 |
| 4,964,409 | 10/1990 | Tremulis | 128/657 |
| 4,977,901 | 12/1990 | Ofstead | 128/772 |
| 5,001,009 | 3/1991 | Whitbourne. | |
| 5,023,114 | 6/1991 | Halpern et al. | 427/2.24 |
| 5,037,677 | 8/1991 | Halpern et al. | 427/338 |
| 5,069,899 | 12/1991 | Whitbourne et al. | |
| 5,080,893 | 1/1992 | Goldberg et al. | 514/57 |
| 5,106,615 | 4/1992 | Dikstein | 424/78.04 |
| 5,135,516 | 8/1992 | Sahatjan et al. | 427/2.24 |
| 5,217,026 | 6/1993 | Stoy et al. | 128/772 |
| 5,242,428 | 9/1993 | Palestrant | 604/265 |
| 5,253,653 | 10/1993 | Daigle et al. | 128/772 |
| 5,331,027 | 7/1994 | Whitbourne | 524/37 |
| 5,333,620 | 8/1994 | Moutafis et al. | 128/772 |
| 5,365,942 | 11/1994 | Shank | 128/772 |
| 5,379,779 | 1/1995 | Rowland et al. | 128/772 |
| 5,415,639 | 5/1995 | VandeEinde et al. | 604/283 |
| 5,416,131 | 5/1995 | Wolff et al. | 523/105 |
| 5,442,727 | 8/1995 | Gagnon | 210/490 |
| 5,443,455 | 8/1995 | Hergenrother et al. | 428/380 |
| 5,452,726 | 9/1995 | Burmeister et al. | 128/772 |
| 5,454,373 | 10/1995 | Koger et al. | 128/662.06 |
| 5,534,287 | 7/1996 | Lukic | 427/2.28 |
| 5,537,729 | 7/1996 | Kolobow | 427/2.3 |
| 5,549,109 | 8/1996 | Samson et al. | 128/642 |
| 5,585,361 | 12/1996 | Burns et al. | 514/25 |
| 5,772,609 | 6/1998 | Nguyen et al. | 600/585 |
| 5,776,611 | 7/1998 | Elton et al. | 427/435 |
| 5,840,046 | 11/1998 | Deem | 600/585 |
| 5,843,156 | 12/1998 | Slepian | 623/1 |

FOREIGN PATENT DOCUMENTS

| | | |
|---|---|---|
| 0661073 A1 | 12/1991 | European Pat. Off. . |
| 0591091 A1 | 4/1994 | European Pat. Off. . |
| 0661072 A1 | 7/1995 | European Pat. Off. . |
| WO 91/19756 | 12/1991 | WIPO . |
| WO 93/10827 | 6/1993 | WIPO . |

*Primary Examiner*—Diana Dudash

[57] ABSTRACT

A guidewire comprises a core wire having a coil tip at its distal end. The coil tip includes a helically wound filament having adjacent turns spaced apart by a preselected distance. The guidewire is coated with a polymeric material, typically a hydrophilic polysaccharide, such as hyaluronic acid or chondroitin sulfate. By properly selecting the spacing between adjacent turns of the coil tip, the hydrophilic coating will adhere to the coil tip in a manner which does not penetrate the coil and which does not significantly interfere with flexibility and bendability of the coil tip.

17 Claims, 3 Drawing Sheets

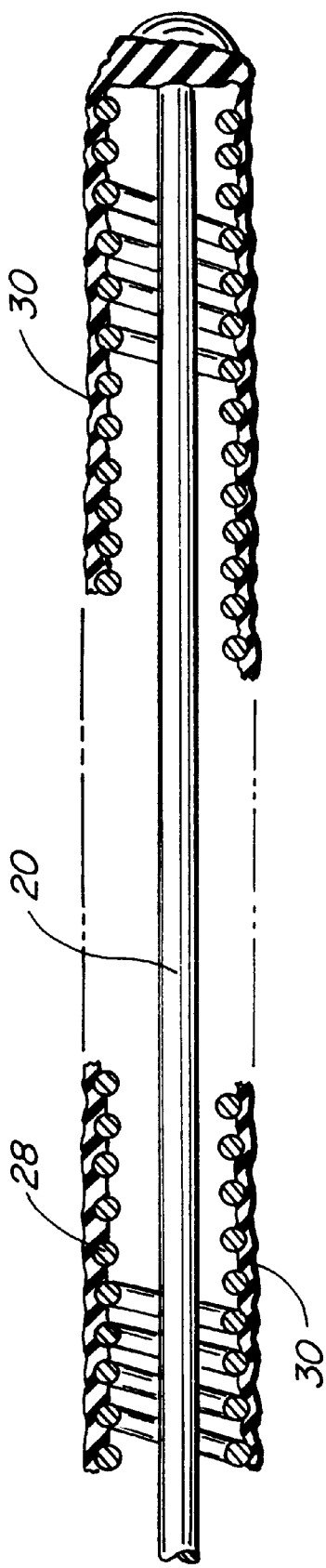
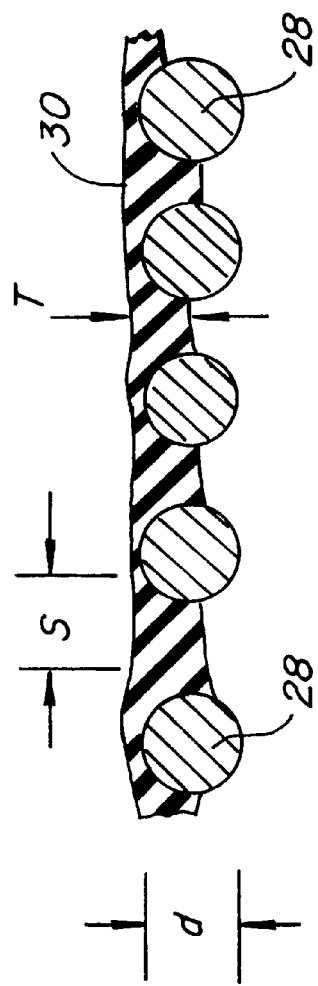
FIG. 2.
FIG. 2A.

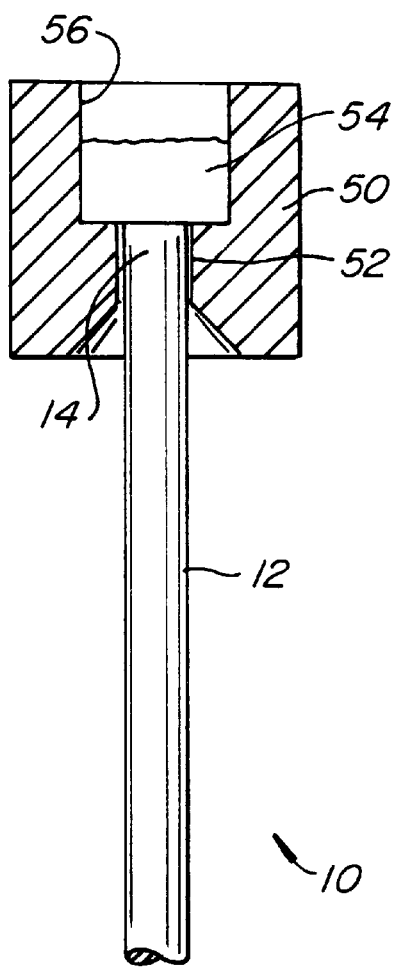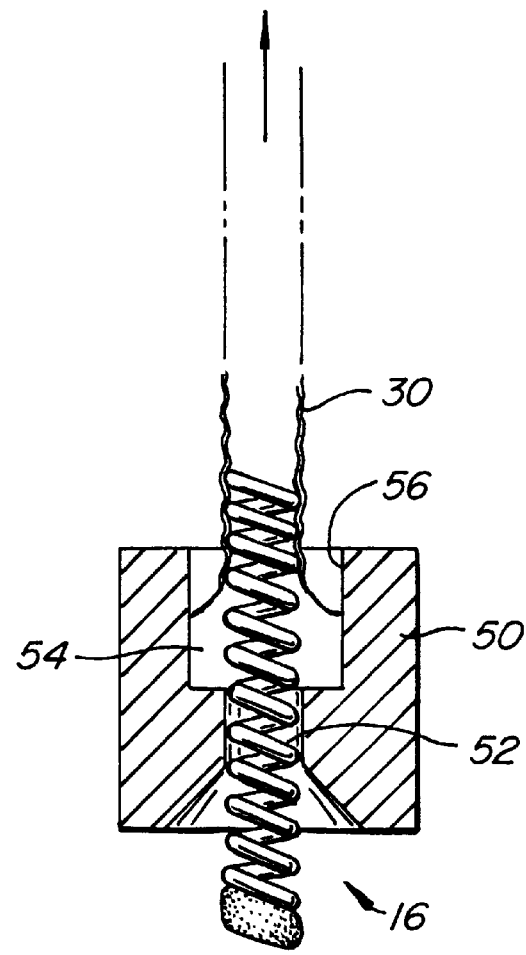
FIG. 3.
FIG. 4.

GUIDEWIRE HAVING HYDROPHILIC COATING

This application is a continuation of, and claims the benefit of priority from U.S. patent application Ser. No. 08/665,973, filed on Jun. 21, 1996, now U.S. Pat. No. 5,840,046 the full disclosure of which is incorporated herein by reference.

BACKGROUND OF THE INVENTION

1. Field of the Invention

The present invention relates generally to medical guidewires. More particularly, the present invention relates to guidewires having hydrophilic coatings and methods for their fabrication.

Medical guidewires are used in a variety of procedures for guiding catheters and other devices to target sites within a patient's body. Of particular interest to the present invention, intravascular guidewires are used for the percutaneous introduction and guiding of both diagnostic and therapeutic catheters within a patient's vasculature. Such intravascular guidewires typically comprise a core wire formed from stainless steel, nickel-titanium alloy, tantalum, or other metals, and a coil tip disposed over the distal end of the core wire. The coil tip is typically a helically wound filament composed of a malleable metal which can be shaped by the physician in order to facilitate placement within the vasculature. After an initial puncture or cut-down is provided into the femoral or other access artery, the guidewire is advanced to the target location by pushing from the proximal end. The guidewire can also be twisted from the proximal end to properly position the bent or deflected coil tip in order to steer the guidewire through arterial junctions.

Guidewires have usually been coated with certain materials in order to facilitate placement through the vasculature. Initially, silicone, PTFE, and other lubricous (but non-hydrophilic) materials were applied both to the core wire and the coil tip in order to reduce friction between the guidewire and adjacent surfaces as the guidewire is introduced.

More recently, guidewires have been coated with hydrophilic materials which have proved to be superior to the earlier non-hydrophilic coatings discussed above. Hydrophilic coatings can trap a thin film of water on the surface of the guidewire, and the water film can prevent direct contact between guidewire and the vasculature and/or catheters which are introduced over the guidewire. Hydrophilic coatings are also more durable than the silicone coatings used previously.

While a significant advance in the design of guidewires, hydrophilic coatings suffer from certain drawbacks. In particular, hydrophilic coatings have generally not been applied to the coil tips of guidewires since they have a tendency to bind the coils together, rendering the coil too stiff and brittle for use. Thus, the advantages of hydrophilic coatings have been unavailable on the distal tip of the guidewire, where low surface friction is critical.

For these reasons, it would be desirable to provide improved guidewire designs and methods for their fabrication. In particular, it would be desirable to provide guidewires having coil tips, where the entire length of the guidewire including the coil tip is coated with hydrophilic coating. It would be particularly desirable if the hydrophilic coating on such guidewires would not significantly reduce the flexibility and shapeability of the coil tip. The methods for fabricating the wire should be relatively simple, compatible with a wide variety of hydrophilic materials, and result in hydrophilic coating having appropriate thicknesses and properties which are compatible with the intended use of the guidewire. At least some of these objectives will be addressed by the invention as described below.

2. Description of the Background Art

Guidewires comprising a core wire and a distal coil tip are described in U.S. Pat. Nos. 5,365,942; 4,964,409; 4,846,186; 4,748,986; 4,554,929; and 4,545,390. The '942, '186, and '929 patents each disclose coil tips having spaced-apart turns.

Catheters and guidewires having hydrophilic coatings are disclosed in U.S. Pat. Nos. 5,454,373; 5,443,455; 5,416,131; 5,242,428; 5,217,026; and 5,135,516; PCT Publications WO 93/10827 and WO 91/19756; and European Publications EP 661 072; and EP 591 091.

Guidewires which are encapsulated in plastic sleeves are disclosed in U.S. Pat. Nos. 5,452,726 and 5,333,620; and EP 661 073.

Methods and materials for hydrophilic coating of medical and other devices are described in U.S. Pat. Nos. 5,331,027; 5,067,899; 5,037,677; 5,001,009; 4,959,074; 4,801,475; and 4,663,233.

SUMMARY OF THE INVENTION

Guidewires according to the present invention comprise a core wire having a proximal end, a distal end, and a shapeable coil disposed over a distal portion of the core wire. The coil comprises a helically wound filament having a plurality of successive turns which are spaced-apart by a distance in the range from 15% to 50% of the width of the filament. A polymeric coating is placed over at least the coil tip and bridges the space between successive turns of the helical element.

The polymeric coating is preferably a hydrophilic polymer, e.g. a polyolefin such as polyvinylpyrrolidone and/or a polysaccharide such as hyaluronic acid or chondroitin sulfate, and it has been found that the spacing between adjacent turns of the coil allows the coating to flex and accommodate bending of the coil without significant loss of pliability. In particular, such spacing allows the coil tip to be coated without penetration of the coating material into the annular space between the coil and the internal core wire. Coil spacings significantly below the 15% value generally do not allow the polymeric coating to flex as the coil is deformed, and spacing greater than the 50% value can allow penetration of the coating material, which similarly inhibits flexing of the coil tip.

In the exemplary embodiment, the coil filament has a circular cross-section with a diameter in the range from about 0.02 mm to 0.1 mm and a spacing between adjacent turns in the range from about 0.003 mm to 0.05 mm. The thickness of the polymeric coating, typically a polysaccharide coating, is in the range from about 0.025 $\mu$m to 0.5 mm, usually from 0.05 $\mu$m to 1 $\mu$m. The coil tip may be formed from conventional coil materials, such as platinum, platinum-iridium alloys, gold, stainless steel, tantalum, and the like.

The present invention further provides a method for coating guidewires with hydrophilic and other polymeric coating materials. The guidewire is passed upwardly through a reservoir having an aperture in the bottom. The coating solution is introduced into the reservoir prior to or as the guidewire is passed therethrough. The viscosity of the coating solution and rate at which the guidewire is passed through the reservoir are controlled so that a thin layer of the coating solution adheres to the outer surface of the guidewire, typically in the ranges set forth above. The coating solution is then heated or otherwise cured to provide the hydrophilic or other coating on the outer surface of the guidewire. This method is particularly suitable for coating the guidewires described above.

BRIEF DESCRIPTION OF THE DRAWINGS

FIG. 2 is a detailed view of the coil tip of the guidewire of FIG. 1, shown in section.

FIG. 2A is a more detailed view of the coil tip showing the spacing between adjacent turns of the coil and the thickness of the hydrophilic coating.

FIGS. 3 and 4 illustrate the method of the present invention for coating a guidewire with a hydrophilic or other polymeric material.

DESCRIPTION OF THE SPECIFIC EMBODIMENTS

Figure 1:
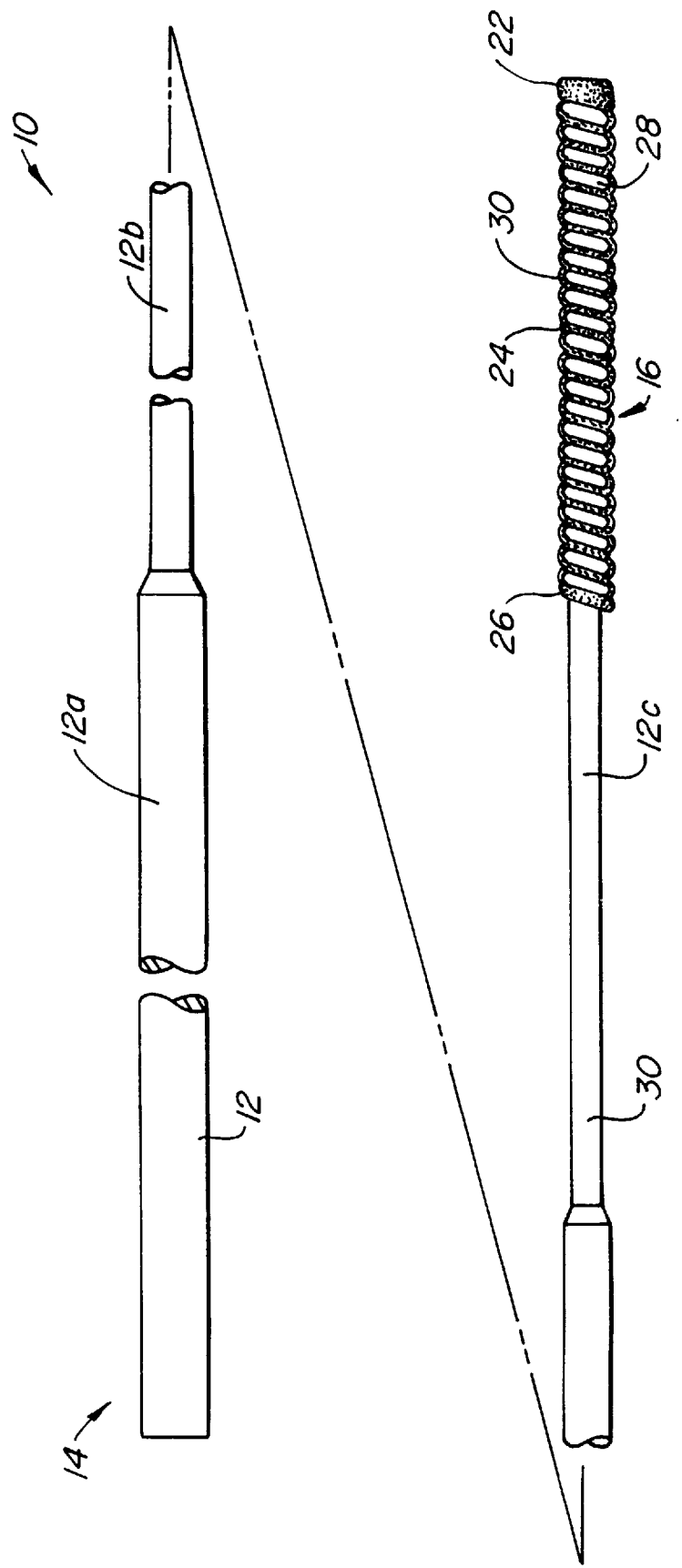
FIG. 1 is a side view of a guidewire constructed in accordance with the principles of the present invention.

The guidewire of the present invention will comprise a core wire and a coil tip disposed over a distal portion of the core wire. The materials, dimensions, and other features of the core wire may be generally conventional. Typically, the core wire will have a length in the range from about 100 cm to 250 cm and a diameter in the range from about 0.2 mm to 0.5 mm. The core wire may be tapered, i.e. have a larger diameter near its proximal end than at its distal end. Often, the tapering will be provided in stages with a series of three or four cylindrical sections joined by conical transition regions. The core wire may be composed of any conventional guidewire material, such as stainless steel, nickel-titanium alloy, tantalum, or combinations or alloys thereof. The exemplary material for forming the guidewire of the present invention is stainless steel.

The coil will extend over a length in the range from about 4 cm to 30 cm at the distal end of the core wire. Typically, the diameter of the core wire at the distal end will be significantly less than the internal diameter of the coil, leaving an annular gap between the core wire and the inner surface of the coil. The coil will typically be joined to the core wire by soldering at at least the distal and proximal ends of the core wire, and usually at at least one location intermediate the two ends. The coil will usually be formed by winding a monofilament of a malleable metal over a mandrel and thereafter securing the coil to the core wire. The present invention may utilize any conventional coil material, such as platinum, platinum-iridium alloy, stainless steel, tantalum, gold, and combinations and alloys thereof. Use of the malleable coil materials permits the coil tip to be shaped into a desired geometry prior to use.

As described thusfar, the construction of the core wire and coil tip has been generally conventional. The present invention, however, provides for modified coil tip designs which facilitate the application of polymeric coatings (preferably hydrophilic polymeric coatings) without substantial or significant loss of flexibility and bendability of the coil tip. In particular, the present invention provides for a particular pattern of spacing between adjacent turns of the coil tip so that particular polymeric materials, such as polyolefins, polysaccharides, and other suitable hydrophilic and non-hydrophilic polymers, may be applied to the tip to coat the tip without significantly inhibiting the flexibility and shapeability of the coil tip. In particular, the adjacent turns of the coil tip should be spaced apart from each other by a distance in the range from about 15% to 50% of the filament width, preferably in the range from 25% to 30% of the filament width. The filament will typically have a circular cross-section and a diameter in the range from 0.02 mm to 0.1 mm, and the preferred spacing between turns is in the range from 0.01 mm to 0.05 mm. Coils having these dimensions have been found to accept hydrophilic coatings without significant loss of flexibility and shapeability.

After the coil tips, as described above, are secured over the distal ends of the core wires, it is necessary to coat the resulting assemblies with the desired hydrophilic materials. A wide variety of hydrophilic polymers are available and described in the medical and patent literature. In particular, the present invention can utilize the materials described in U.S. Pat. Nos. 5,331,027; 5,067,899; 5,037,677; 5,001,009; 4,959,074; 4,801,475; and 4,663,233, the full disclosures of which are incorporated herein by reference. Preferred is the use of polyvinylpyrrolidone (PVP) as described in U.S. Pat. Nos. 5,331,027; 5,069,899; and 5,001,009. A particularly preferred PVP coating is available under the tradename SLIP-COAT from STS Biopolymers of Henrietta, N.Y. Others are available from BioCoat, Inc. of Fort Washington, Pa. Other suitable polymers include hydrophilic polysacchrides, particularly hyaluronic acid, chondroitin sulfate, and other equivalent glycosaminoglycans. These materials may be applied by spraying, wiping, immersion, or other means, so long as appropriate measures are taken to provide a proper coating thickness, typically in the range from 0.025 $\mu$m to 0.5 mm, usually from 0.05 $\mu$m to 1 $\mu$m, and to avoid penetration of the materials into the annular space between the coil tip and the core wire. A particularly preferred method for coating these materials onto the guidewires of the present invention is set forth below.

The guidewire assemblies including the core wire and coil tip may be coated by passing the guidewires upwardly through a reservoir containing a liquid coating solution comprising the polymer. An exemplary PVP coating solution has a relatively high viscosity, preferably in the range from 20 cp to 300 cp, preferably in the range from 50 cp to 250 cp. Viscosities in this range help prevent penetration of the coating material through the coil into the annular base between the coil and the core wire. Additionally, the guidewire will be drawn vertically upward through the reservoir containing the coating solution at a controlled rate selected to provide for the desired thickness of the coating material onto the guidewire surface without penetration of the coating material through the coil tip. Typically, the guidewire will be drawn upwardly at a rate in the range from 0.1 cm/sec to 30 cm/sec, usually from 1 cm/sec to 20 cm/sec. Preferably, the guidewire will be drawn upwardly using a motorized system where the rate can be controlled precisely.

After coating the guidewire with the liquid coating material, the liquid will be cured to provide a permanent layer of hydrophilic or other polymeric materials on the guidewire. For the exemplary PVP coating solution, the polymeric layer is cured in an oven at a temperature in the range from 40° C. to 200° C. for a time from 15 minutes to 24 hours.

Referring now to FIG. 1, a guidewire 10 comprises a core wire 12 having a proximal end 14 and a coil tip 16 at its distal end. The core wire 12 is tapered in a series of cylindrical sections 12a, 12b, and 12c having reduced diameters. The core wire 12 is disposed over a final section 20 (FIG. 2) typically having a diameter in the range from 0.2 mm to 0.9 mm. The coil tip 16 is secured to the core wire section 20 by soldering in at least three locations 22, 24, and 26 and comprises a metal filament 28 which is helically wound into a plurality of successive turns, as best observed in FIGS. 2 and 2A. The filament 28 will typically have a circular cross-section with a diameter d (FIG. 2A) in the range from 0.02 mm to 0.1 mm. The spacing S (FIG. 2A) between adjacent turns will be within the ranges set forth above, typically being from 0.003 mm to 0.05 mm. A hydrophilic coating 30 will be applied over the entire length of the guidewire 10, as described in more detail below. The coating 30 will typically have a thickness T in the range from 0.025 $\mu$m to 0.5 mm, usually from 0.05 $\mu$m to 1 $\mu$m, as illustrated in FIG. 2A.

The coating 30 is preferably applied by the method illustrated in FIGS. 3 and 4. A reservoir 50 includes an aperture 52 in a lower surface thereof. The guidewire 10 may be passed upwardly through the aperture 52, typically with the proximal end 14 passing through the aperture 52 first, as shown in FIG. 3. A volume of coating solution 54 is placed in a well 56 of the reservoir 50. A sufficient amount of the coating solution 54 may be placed in the well 56 initially, or the solution may be added continuously as the guidewire 10 is drawn upwardly through the reservoir 50.

As shown in FIG. 4, the coil tip 16 will usually pass through the reservoir 50 at the end of the coating procedure. The coating solution 54 will adhere to the outer surface of the coil filaments 28 but will not penetrate through the spaces between adjacent turns of the coil filament. By properly controlling the viscosity of the coating solution 54, the rate at which the guidewire is drawn through the reservoir 50, the temperature (which is typically room temperature), and the like, a liquid layer of the coating material having a desired thickness as set forth above can be applied uniformly over the entire length of the guidewire.

After removing the guidewire 10 from the coating reservoir 50, the liquid film may be cured to produce the final hydrophilic layer on the guidewire, as described above.

Although the foregoing invention has been described in some detail by way of illustration and example, for purposes of clarity of understanding, it will be obvious that certain changes and modifications may be practiced within the scope of the appended claims.

What is claimed is:

1. A method for coating a guidewire, said method comprising:

providing a guidewire having a proximal end and a distal coil comprising a wound filament having a plurality of successive spaced apart turns;

providing a reservoir having an aperture in a bottom surface thereof;

introducing a coating solution into the reservoir;

passing the guidewire upwardly through aperture so that a layer of the coating solution adheres to the outer surface of the guidewire; and curing the coating solution to form a hydrophilic coating on the outer surface of the guidewire.

2. A method as in claim 1, wherein the distal coil of the guidewire comprises a wound filament having a plurality of successive, spaced-apart turns, wherein the coating step comprises passing the coil through the aperture at a rate which results in bridging of the coating solution between the successive turns and inhibiting penetration of the coating solution to the interior of the coil.

3. A method as in claim 2, wherein the proximal end of the guidewire is passed through the aperture first.

4. A method as in claim 1, wherein the coating solution comprises a hydrophilic polymer.

5. A method as in claim 4, wherein the hydrophilic polymer is a polysaccharide selected from the group consisting of hyaluronic acid and chondroitin sulfate.

6. A method as in claim 5, wherein the solution is applied at room temperature where it has a viscosity in the range from 20 cp to 300 cp.

7. A method as in claim 6, wherein the guidewire is passed upwardly at a rate in the range from 0.1 cm/sec to 30 cm/sec.

8. A method as in claim 1, wherein the coating solution is applied to a thickness in the range from 0.025 $\mu$m to 0.5 mm.

9. A method as in claim 1, wherein the curing step comprises heating to a temperature in the range from 40° C. to 200° C. for a period of time from 15 minutes to 24 hours.

10. A method for coating a guidewire, said method comprising:

providing a guidewire having a proximal end and a distal coil;

providing a reservoir having an aperture in a bottom surface thereof;

introducing a coating solution into the reservoir, said coating solution selected from the group consisting of a polyvinylpyrrolidone or a polysaccharide;

passing the guidewire upwardly through aperture so that a layer of the coating solution adheres to the outer surface of the guidewire; and curing the coating solution to form a hydrophilic coating on the outer surface of the guidewire.

11. A method as in claim 10, wherein the distal coil of the guidewire comprises a wound filament having a plurality of successive, spaced-apart turns, wherein the coating step comprises passing the coil through the aperture at a rate which results in bridging of the coating solution between the successive turns and inhibiting penetration of the coating solution to the interior of the coil.

12. A method as in claim 11, wherein the proximal end of the guidewire is passed through the aperture first.

13. A method as in claim 10, wherein the hydrophilic polymer is a polysaccharide selected from the group consisting of hyaluronic acid and chondroitin sulfate.

14. A method as in claim 13, wherein the solution is applied at room temperature where it has a viscosity in the range from 20 cp to 300 cp.

15. A method as in claim 14, wherein the guidewire is passed upwardly at a rate in the range of 0.1 cm/sec to 30 cm/sec.

16. A method as in claim 10, wherein the coating solution is applied to a thickness in the range from 0.025 $\mu$m to 0.5 mm.

17. A method as in claim 10, wherein the curing step comprises heating to a temperature in the range from 40° C. to 200° C. for a period of time from 15 minutes to 24 hours.

* * * * *